United States Patent
Lourdusamy et al.

(10) Patent No.: US 9,487,496 B2
(45) Date of Patent: Nov. 8, 2016

(54) PROCESS FOR THE PREPARATION OF CABAZITAXEL AND ITS INTERMEDIATES

(71) Applicant: INTAS PHARMACEUTICALS LIMITED, Ahmedabad (IN)

(72) Inventors: Mettilda Lourdusamy, Quebec (CA); Ioan Iosif Radu, Quebec (CA); Rahul Chandrashayi Saxena, Ahmedabad (IN); Raghvendra Jayantibhai Patel, Ahmedabad (IN); Sandeep Bachubhai Shah, Ahmedabad (IN)

(73) Assignee: Intas Pharmaceuticals Limited, Ahmedabad (IN)

( * ) Notice: Subject to any disclaimer, the term of this patent is extended or adjusted under 35 U.S.C. 154(b) by 0 days.

(21) Appl. No.: 14/441,726

(22) PCT Filed: Oct. 31, 2013

(86) PCT No.: PCT/IN2013/000669
§ 371 (c)(1),
(2) Date: May 8, 2015

(87) PCT Pub. No.: WO2014/072996
PCT Pub. Date: May 15, 2014

(65) Prior Publication Data
US 2015/0307468 A1    Oct. 29, 2015

(30) Foreign Application Priority Data
Nov. 9, 2012 (IN) .......................... 3256/MUM/2012

(51) Int. Cl.
*C07D 305/00* (2006.01)
*C07D 305/14* (2006.01)

(52) U.S. Cl.
CPC ................... *C07D 305/14* (2013.01)

(58) Field of Classification Search
CPC ..................................... C07D 305/14
USPC ........................................ 549/510
See application file for complete search history.

(56) References Cited

U.S. PATENT DOCUMENTS

| | | | |
|---|---|---|---|
| 5,635,531 A | 6/1997 | Chen | |
| 5,847,170 A | 12/1998 | Bouchard et al. | |
| 5,962,705 A | 10/1999 | Didier et al. | |

FOREIGN PATENT DOCUMENTS

| | | | |
|---|---|---|---|
| CN | 102060815 | | 5/2011 |
| CN | 102285947 | * | 12/2011 |
| CN | 102417491 | * | 4/2012 |

OTHER PUBLICATIONS

Evans, et al., "Mild Alcohol Methylation Procedures for the Synthesis of Polyoxygenated Natural Products. Applications to the Synthesis of Lonomycin A", Tetrahedron Letters, vol. 35, No. 39, pp. 7171-7172, Jan. 1, 1994.
International Search Report issued in PCT International Application No. PCT/IN2013/000669, mailed Jul. 22, 2014.

* cited by examiner

*Primary Examiner* — T. Victor Oh
(74) *Attorney, Agent, or Firm* — Hamre, Schumann, Mueller & Larson, P.C.

(57) ABSTRACT

The present invention relates to a novel process for preparation of cabazitaxel (I) starting from 10-Deacetyl baccatin or derivative that involves methylation of 7, 10 —OH groups. Also provided is a novel process using chiral bis-lactam linker for the synthesis of cabazitaxel.

20 Claims, No Drawings

PROCESS FOR THE PREPARATION OF CABAZITAXEL AND ITS INTERMEDIATES

FIELD OF THE INVENTION

The present invention relates to a novel process for the preparation of Cabazitaxel and its intermediates.

BACKGROUND OF THE INVENTION

Cabazitaxel exhibits notable anticancer and antileukaemic properties. Cabazitaxel, chemically known as 4-acetoxy-2α-benzoyloxy-5β,20-epoxy-1-hydroxy-7β 10β-dimethoxy-9-oxo-tax-11-en-13α-yl(2R,3S)-3-tert-butoxycarbonylamino-2-hydroxy-3-phenylpropionate and is represented by the following structural formula:

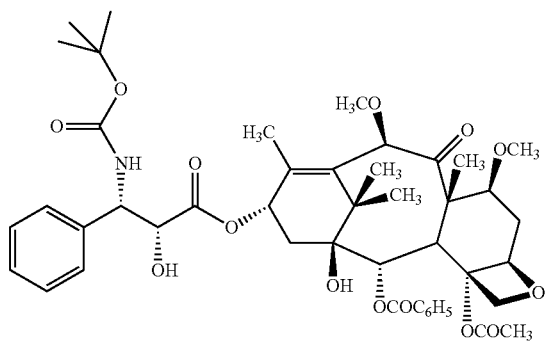

(I)

The compound was disclosed in U.S. Pat. No. 5,847,170 (hereinafter referred as US' 170). It is sold under brand name Jevtana as its acetone solvate. Cabazitaxel is prepared according to the method which is described more particularly in US' 170.

Although Cabazitaxel is a very important second line treatment for the metastatic CRPC, there are still limited reports on the synthesis of Cabazitaxel. Aventis reported the first synthetic route of Cabazitaxel in US' 170 starting from 10-deacetylbaccatin III (10-DAB). The synthesis consisted of more than five steps with a very low reported yield.

U.S. Pat. No. 5,962,705 disclosed a process for the taxoid derivatives using alkylating agents such as alkyl halide, alkyl sulfate, oxonium in the presence of an anionization agent.

CN 102060815 provided a method for the conversion of Docetaxel to Cabazitaxel by using dimethylsulfate as an alkylating agent in a weakly alkaline organic solvent (pyridine).

CN 102285947 reported the synthesis of Cabazitaxel by methylating the 7 and 10-OH in 10-DAB simultaneously to furnish 7,10-dimethyl-10-DAB, which was then coupled with a protected (3R,4S)-β-lactam followed by deprotection of the 2'-OH, the total yield is approximately 18.0% for 3 steps.

Thus, there is a need for developing a process for preparation of cabazitaxel and its key intermediates which is not only feasible at industrial scale but also meets economics of scale in terms of yield.

OBJECTS OF THE INVENTION

It is an object of the present invention is to provide a novel process for the preparation of Cabazitaxel and its key intermediate.

Another object of the present invention is to provide a process for preparing Cabazitaxel using chiral auxiliaries.

Another object of the present invention is to provide a process for preparing Cabazitaxel from Docetaxel.

SUMMARY OF THE INVENTION

In one aspect the present invention provides a process for preparation of cabazitaxel (I) comprising methylation of compound of formula (II)

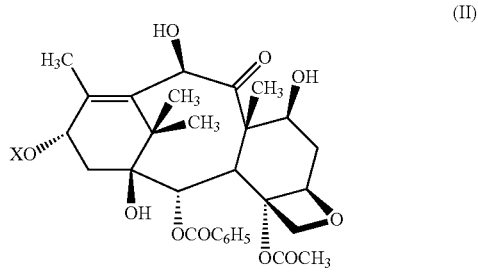

(II)

in which X represents H or side chain of formula (III)

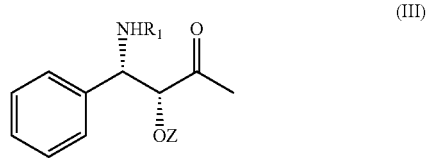

(III)

Z represents a hydroxy protecting group, R1 is $C(O)OC(CH_3)_3$,

Using a methylating agent, methyl trifluoromethansulfonate to get compound of formula (IV)

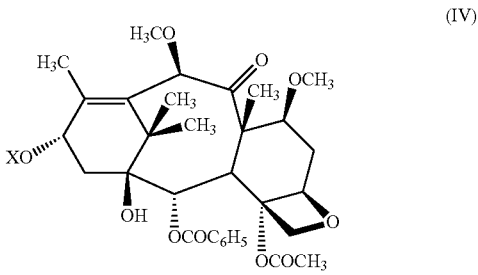

(IV)

converting, compound of formula (IV) to cabazitaxel (I).

Yet another aspect of the present invention provides process to prepare cabazitaxel (I) comprising reacting a compound of formula (II) wherein Z=triethyl silyl with methyl trifluoromethansulfonate to obtain compound of formula (XII)

(XII)

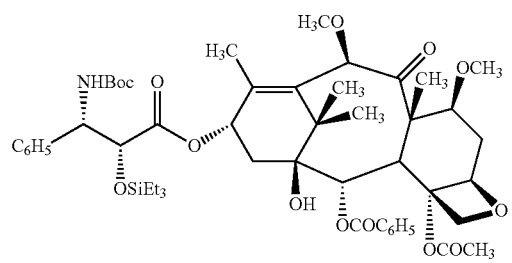

converting compound of formula (XII) to cabazitaxel

In another aspect the present invention provides a process to prepare cabazitaxel (I) comprising selective 2' deprotection of compound of formula (XIII)

(XIII)

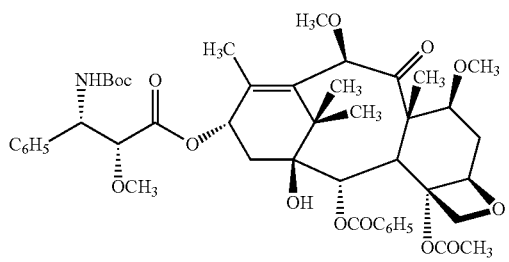

In accordance with another aspect of the present invention there is provided a process for preparation of cabazitaxel where novel and chiral bis lactam of formula (V)

(V)

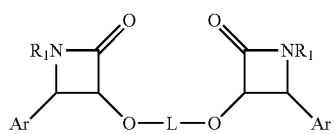

R1 is defined above, Ar is a phenyl group and L is a cleavable linker
is reacted with a suitable taxane precursor of formula (VI)

(VI)

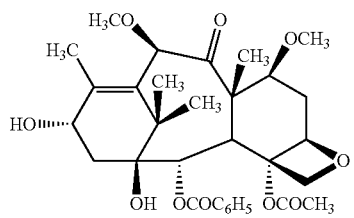

to give a compound of formula (VII)

(VII)

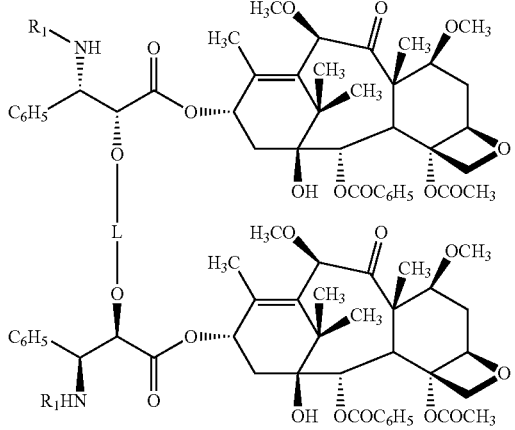

cleaving the linker from compound of formula (VII) to get cabazitaxel (I).

In a further aspect the present invention provides a process to prepare cabazitaxel which comprises reacting compound of formula (VIII)

(VIII)

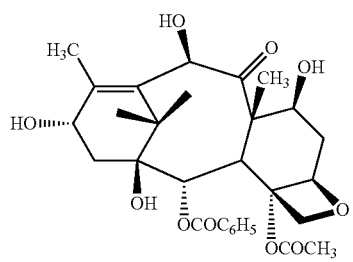

with methyl trifluorornethansulfonate to obtain compound of formula (VI)

(VI)

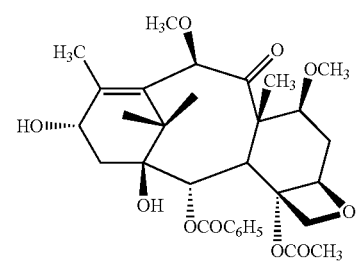

reacting compound of formula (VI) with compound of formula (IX)

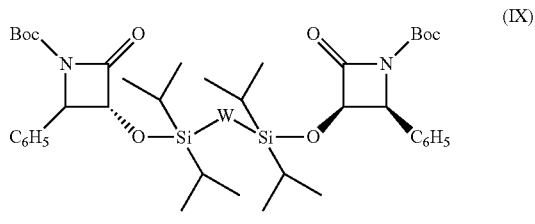

(IX)

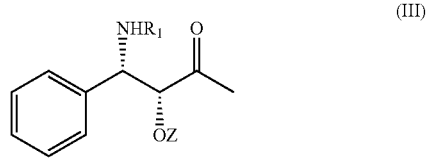

(III)

BOC=CO(O)C(C+H3)₃, W=alkyl of 1-30 carbon atom to get compound of formula (X)

wherein Z represents hydroxy protecting group and R1 is C(O)OC(CH3)₃, using methyl trifuoromethanesulfonate as methylating agent. This process includes direct conversion of docetaxel to cabazitaxel or methylation of 10-deacetyl baccatin and further conversion of 7,10 dimethyl baccatin to cabazitaxel.

More specifically, according to one of the aspects of the present invention, processes for preparation of cabazitaxel using docetaxel are described.

Accordingly, in an embodiment the present invention provides a process to prepare cabazitaxel wherein compound of structural formula (XI)

(X)

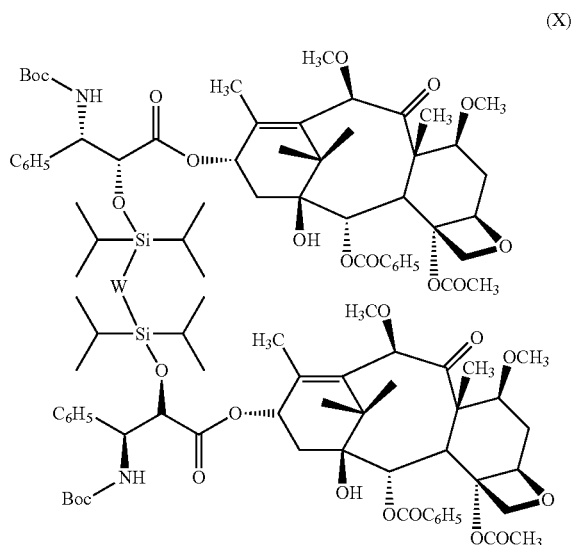

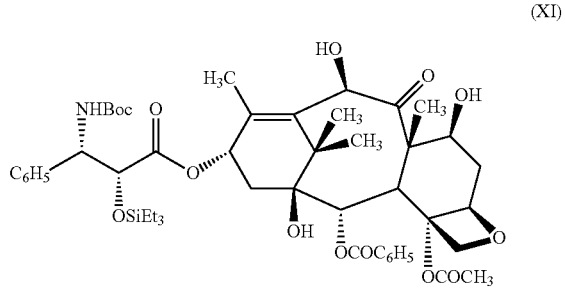

(XI)

converting compound of formula (X) to cabazitaxel (I)

DETAILED DESCRIPTION

The present invention provides process for preparing cabazitaxel.

Accordingly, the present invention provides a process for methylation of the two hydroxyl groups at 7 and 10 position of 10-deacetylbaccatin or derivatives thereof of formula (II)

is reacted with methyl trifluoromethansulfonate to get compound of formula (XII)

(XII)

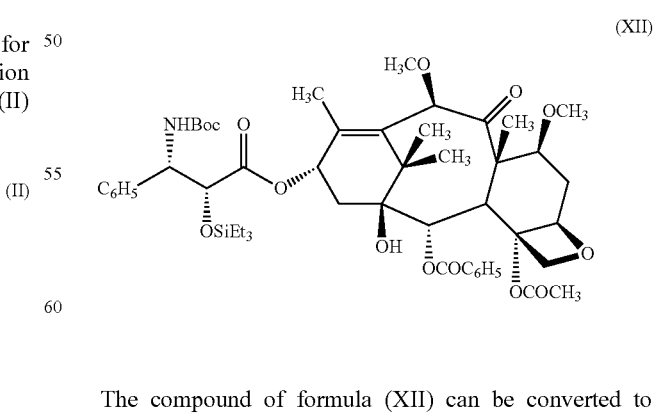

(II)

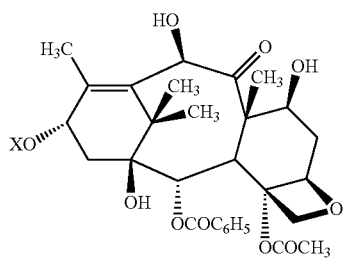

The compound of formula (XII) can be converted to cabazitaxel

The process can be further exemplified as following scheme

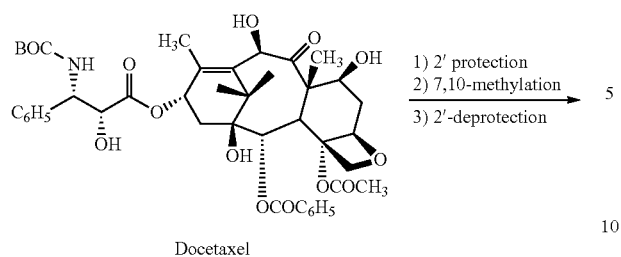

Docetaxel 1) 2' protection
2) 7,10-methylation
3) 2'-deprotection

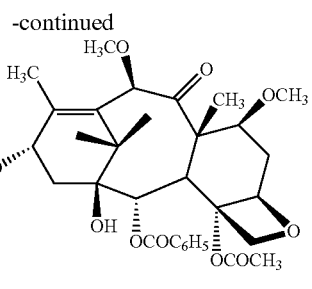

(XIII)

| selective, 2' deprotection

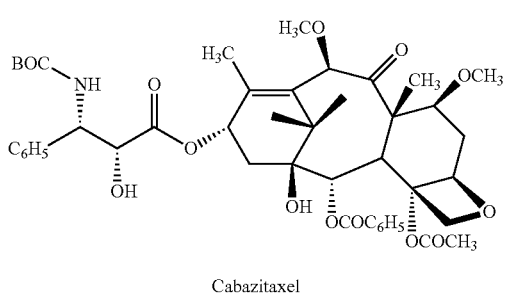

Cabazitaxel

In another aspect the present invention provides a process for preparing cabazitaxel by selective deprotection of compound of formula (XIII)

(XIII)

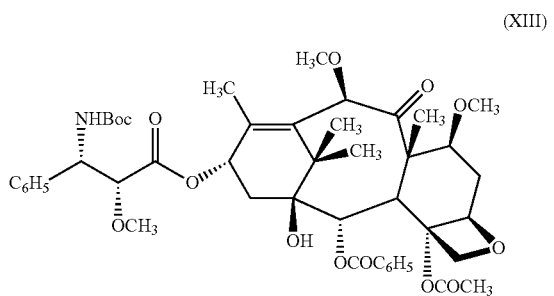

The process can be further exemplified as following-scheme

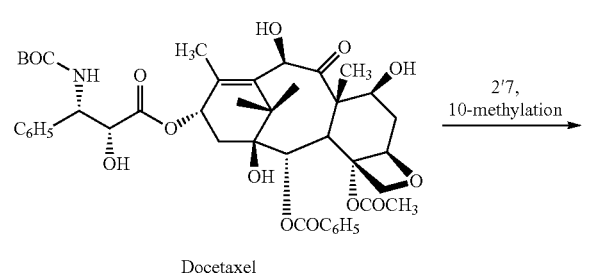

Docetaxel

2'7, 10-methylation

In the process of present invention protecting group can be selected from any suitable hydroxy protecting group preferably a silyl protecting group such as triethyl silyl is used for the purpose of present invention.

The protection reaction or can be carried out in presence of a suitable solvent and base. Solvent can be selected from any suitable solvent such from the group comprising of nitrile, chlorinated hydrocarbon, polar aprotic solvent, ethers and mixture thereof. Base can be selected from inorganic such as alkali metal or alkali earth-metal carbonate or bicarbonates, metal hydroxide, organic base can be selected from group consisting of alkyl amine like triethyl amine, morpholine, pyridine like dimethyl amino pyridine, piperidine or like.

Protection of 2'-OH is followed by methylation of 7 and 10 hydroxyl group. The methylation is carried out by using methyl trifluoromethansulfonate (methyl triflate). The reaction can be carried out in presence of solvent and base. The solvent used in methylation reaction can be selected from any suitable organic solvent such as solvent selected from the class of ester, ketone, ether, cyclic ether or like. The base can be selected from any base suitably used in methylation preferably salts hexamethyldisilazide are used in present process. 2',7,10 methylation can also be carried out in presence of suitable solvent and base.

The protected cabazitaxel thus prepared can be subjected to deprotection or selective deprotection in presence of base. Preferably a mild base such as tetrabutyl ammonium fluoride is used.

The above process of protection of —OH group, methylation and deprotection or 2',7,10 methylation and 2' selective deprotection to get cabazitaxel can be carried out in a single step i.e. without isolating the intermediate stages or in multiple steps.

Another aspect of the present invention is to provide a process for the preparation of Cabazitaxel, where novel, chiral bis-lactams of formula (V)

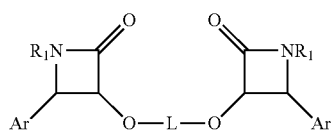

(V)

R1 is defined above, Ar is a phenyl group and L is a cleavable linker is reacted with a suitable taxane precursor having a free C-13 hydroxy group.

Accordingly, cabazitaxel can be prepared by reacting taxane precursor of formula (VI):

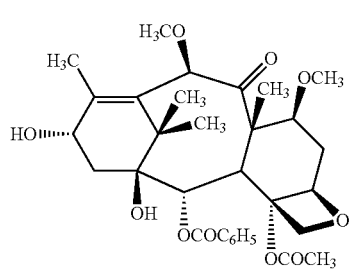

(VI)

with a compound of formula (V) to give a compound of formula (VII)

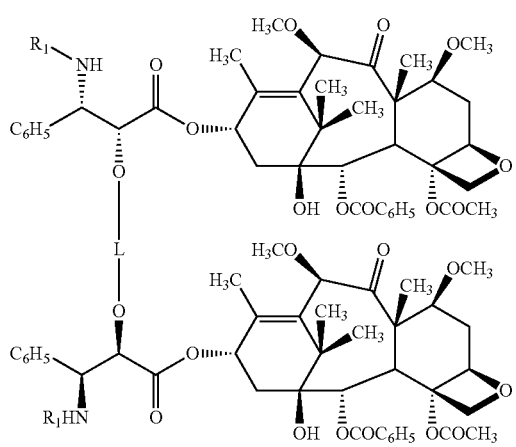

(VII)

Cabazitaxel is released from the compound of formula (VII) by cleaving the linker.

The cleavable linker L can be chiral or non-chiral, preferably selected from the group consisting of hydrolysable ketals, acetals, silyl, esters, diesters and hydrogenolysable benzyl group.

Further L can be selected form compound of structural formula

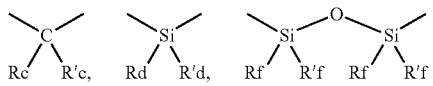

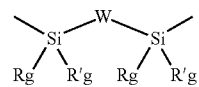

wherein Rc and R'c, identical or different are alkyl, aryl or hydrogen, Rd and R'd, identical or different are alkyl, aryl or hydrogen, Rf and R'f, identical or different are alkyl, aryl or hydrogen, Rg and R'g, identical or different are alkyl, aryl or hydrogen; W is an alkyl. Further W can be an alkyl of 1-30 carbon atoms.

In an embodiment the taxane precursor can be prepared by reacting 10-deacetyl baccatin III of formula (VIII)

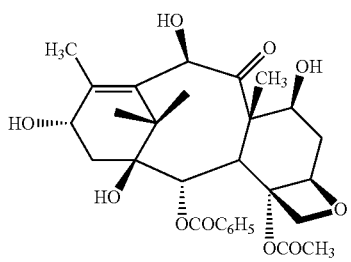

(VIII)

with methylating agent, preferably methyl trifluoromethansulfonate. The methylation reaction is carried out in presence of a base preferably the base used herein is salt of hexamethyl disilazide like sodium, potassium, lithium hexamethyl disilazide. The 7,10-dimethoxy-10-deacetyl baccatin-III (VI) thus prepared

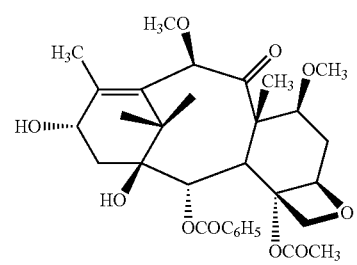

(VI)

is reacted with N-boc-bis lactam of formula (IX)

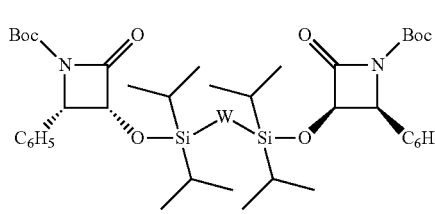

(IX)

BOC=CO(O)C—(CH3), W=alkyl of 1-30 carbon atoms to give compound of formula (X)

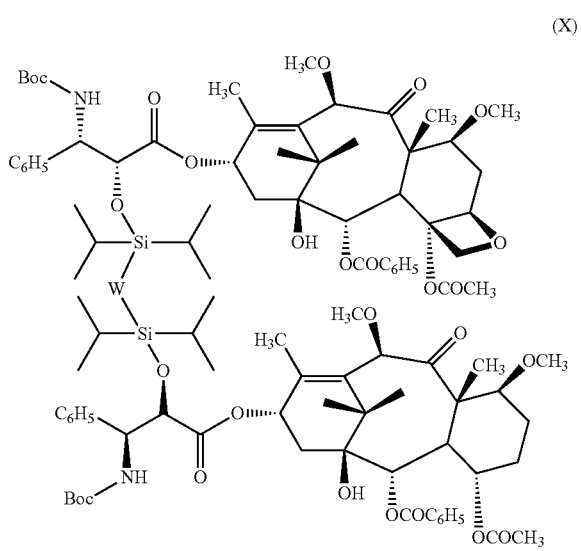

(X)

The reaction, is carried out in presence of a suitable solvent and base. The process comprises reacting in presence of solvent selected from class of ether, cyclic ether, ester, halogenated solvent, hydrocarbon, protic or aprotic solvent. The base can be selected from any suitable base for such reaction preferably the present invention uses salt of hexa methyl disilazide such as sodium potassium or lithium hexamethyl disilazide.

Compound of formula (X) is subjected to a reaction for cleavage of linker to get cabazitaxel. The reaction can be carried out in presence of solvent and base. Solvent can be selected from any suitable solvent like ether such as tetrahydrofuran, ketone such as acetone, ester such as ethyl acetate, alkane such as heptane, alcohol such as isopropyl alcohol, nitrile such acetonitrile or like. The solvent can be used as single solvent, as mixture or as a solvent antisolvent combination thereof.

Cabazitaxel thus obtained can be further purified by treating with solvents, such as acetonitrile, diethyl ether, benzyloxy methyl ether, benzyl ether, petroleum ether, ester such as ethyl acetate, alcohol such as ethanol, methanol, isopropanol either as a single solvent or a mixture of solvents in different ratios, preferably in acetonitrile and an alcohol preferably methanol. Cabazitaxel could also be purified by column chromatography but yields may be at lower side.

Following are the specific examples describing the invention. These examples are not intended to limit the scope of the invention in any way.

EXAMPLES

Example 1

Preparation of (2'-Tes-docetaxel) (XI)

To a mixture of docetaxel (807 mg) in 25 ml of dichloromethane at 0° C. was added dimethylaminopyridine, (122 mg) and triethylamine (0.278 ml) followed by triethyl silyl chloride (150 mg). The product was isolated by extraction followed by evaporation of solvent, purified over silica gel using hexane/acetone as eluent to obtain approximately 800 mg of 2'-Tes-docetaxel, in approximately 90% yield.

Example 2

Preparation of 2'-Tes-7,10 dimethoxy-docetaxel (XII)

To 2'-Tes-docetaxel (500 mg) in 10 ml of THF at −30 to −50° C. was added LiHMDS, (1 ml) and methyl trifluoromethansulfonate (0.120 ml). The product was isolated by extraction followed by evaporation of solvent, purified over silica gel using dichloromethane/methanol as eluent to obtain approximately 464 mg of 2'-Tes-7,10-dimethoxy-docetaxel, in approximately 90% yield Example 3

Preparation of Cabazitaxel (I)

To 2'-Tes-7,10-dimethoxy-Tes-docetaxel (380 mg) in 10 ml of tetrahydrofuran at room temperature was added tetrabutylammoniumfluoride, (800 ul). The product is isolated by extraction and evaporation of solvent, purified over silica gel using dichloromethane/methanol as eluent to obtain approximately 275 mg of Cabazitaxel, in approximately 80% yield.

Example 4

Preparation of 2',7, 10-trimethoxy-docetaxel (XIII)

To Docetaxel (2 g) in 25 ml of tetrahydrofuran at −30 to −50° C. was added LiHMDS, (7.4 ml) and methyl trifluoromethansulfonate (0.815 ml). Followed by extraction and evaporation of solvent, purified over silica gel using dichloromethane/methanol as eluent to obtain approx 1.7 g of 2'7, 10-trimethoxy-docetaxel, in approximately 80% yield Example 5

Preparation of Cabazitaxel (I)

To trimethoxy-Docetaxel (850 mg) in 25 ml of dichloromethane at 0° C. was added aqueous solution of HBr (2 ml) and allowed the reaction to complete, product was isolated by extraction and evaporation of solvent, purified over silica gel using dichloromethane/methanol as eluent to obtain approximately 600 mg of cabazitaxel, in approximately 72% yield Example 6

Preparation of 7,10-dimethoxy-10-deacetyl baccatin III (VI)

Under Argon, 2.43 g of deacetyl baccatin in 50 ml of tetrahydrofuran was cooled to −30 to −50 C followed by the addition of 1.23 ml of Methyl triflate and 9.8 ml of 1M LiHMDS. Product was isolated by extraction followed by evaporation of solvent, purified over silica gel using dichloromethane/methanol as eluent to obtain approximately 2.2 g of 7,10-dimethoxy-deacetyl baccatin, in approximately 87% yield Example 7

Preparation of compound of formula (X)

To 8.2 g, of 7,10-dimethoxy-deacetyl baccatin in a mixture of tetrahydrofuran and dimethylformamide was added 7.363 g N-Boc-bis-lactam and 15 ml of 1 M LiHMDS at −20° C. to −30 C under argon product was isolated by extraction, followed by evaporation of the solvent to afford approximately 17 g of dimer compound of formula (XI).

Example 8

Preparation of Cabazitaxel (I)

To 3 g of the dimer (XI), in 20 ml of tetrahydrofuran, at 0° C. was added 3.8 nil of tetrabutyl ammonium fluoride and left stirring under argon. Product was isolated by extraction followed by evaporation of the solvent to afford approximately 3.17 g of Cabazitaxel.

We claim:

1. A process to prepare cabazitaxel (I) comprising:
methylating a compound of formula II

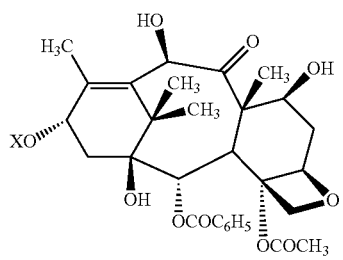

(II)

in which X represents H or a side chain of formula (III)

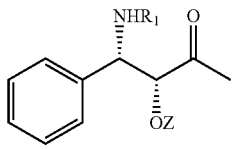

(III)

Z represents a hydroxy protecting group, $R_1$ is —C(O)OC(CH$_3$)$_3$,
with methyl trifluoromethanesulfonate in the presence of a solvent to get a compound of formula (IV)

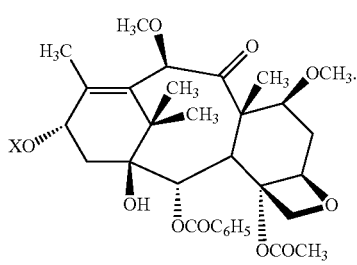

(IV)

2. A process to prepare cabazitaxel comprising:
methylating a compound of formula II

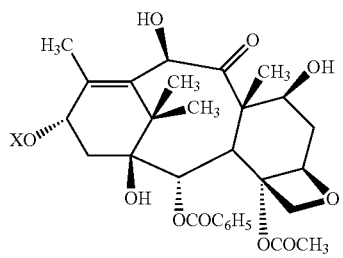

(II)

wherein X represents a side chain of formula (III), Z=triethyl silyl, $R_1$ is —C(O)OC(CH$_3$)$_3$

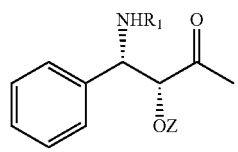

(III)

with methyl trifluoromethanesulfonate in the presence of a solvent to get a compound of formula (XII)

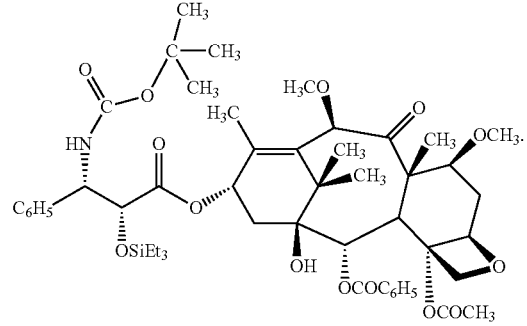

(XII)

3. A process to prepare cabazitaxel comprising:
selective 2' deprotection of a compound of formula (XIII) in the presence of a solvent

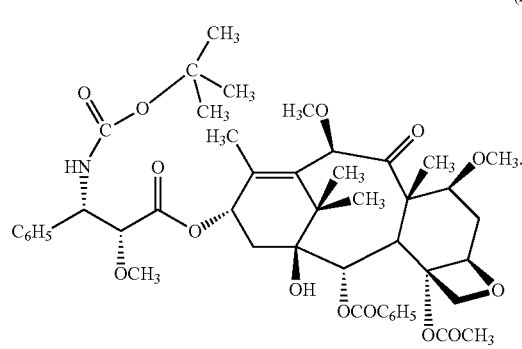

(XIII)

4. A process to prepare cabazitaxel comprising:
reacting a compound of formula (V)

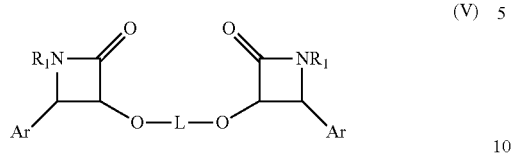

wherein R₁ is —C(O)OC(CH₂)₃, Ar is a phenyl group and L is a cleavable linker with a compound of formula (VI) in the presence of a solvent

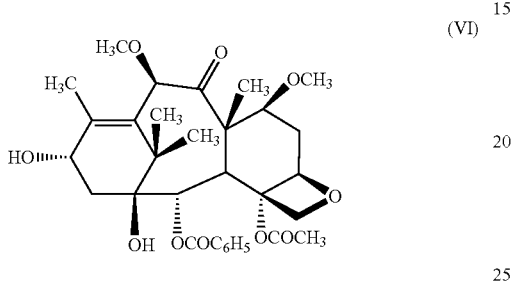

to get a compound of formula (VII)

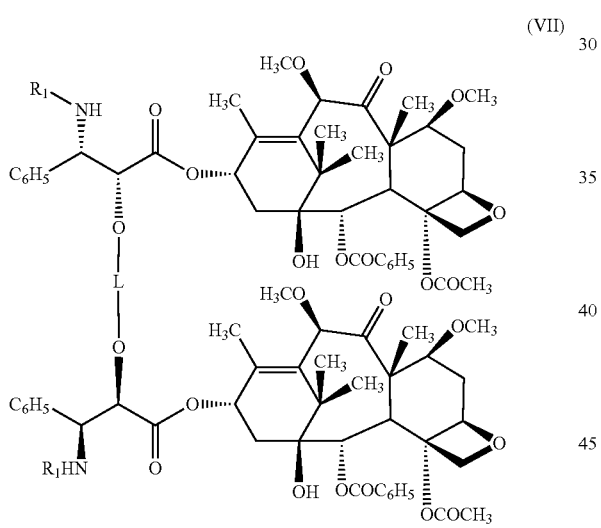

wherein L is selected from a compound having the following structural formula

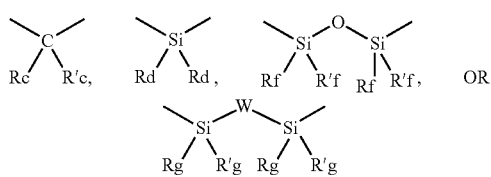

wherein Rc and R'c are identical or different and are alkyl, aryl or hydrogen, Rd and R'd are identical or different and are alkyl, aryl or hydrogen, Rf and R'f are identical or different and are alkyl, aryl or hydrogen, Rg and R'g are identical or different and are alkyl, aryl or hydrogen, and W is an alkyl having 1 to 30 carbon atoms.

5. A process to prepare cabazitaxel comprising:
a. methylating a compound of formula (VIII) with methyl trifluoromethanesulfonate

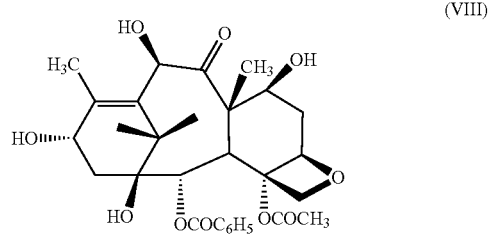

to get a compound of formula (VI);

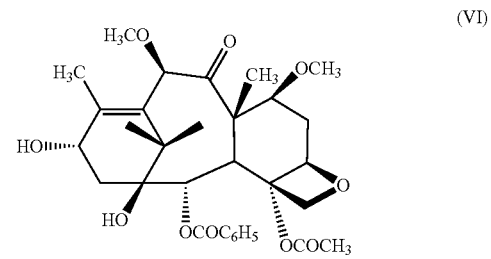

b. reacting a compound of formula (VI) with a compound of formula (IX);

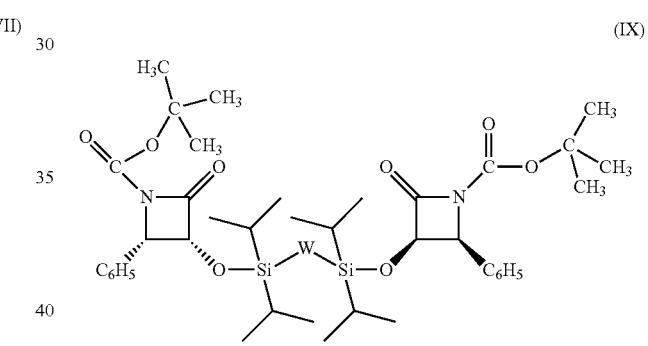

to get a compound of formula (X);

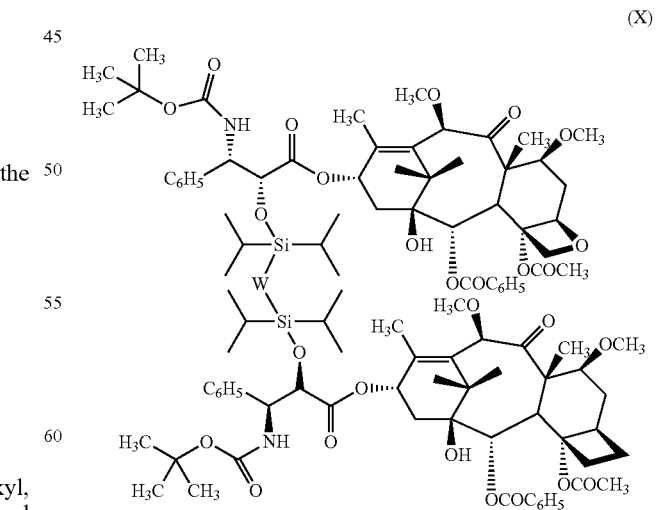

wherein W=alkyl having $C_1$-$C_{30}$,
c. treating a compound of formula (X) in the presence of a solvent and a base to obtain cabazitaxel (I).

6. A process according to claim 1, wherein the solvent is selected from the group consisting of a nitrile, a chlorinated hydrocarbon, a polar aprotic solvent, an ester, an ether, a cyclic ether and mixtures thereof.

7. A process according to claim 1, wherein the methylation is carried in the presence of a base.

8. A process according to claim 7, wherein the base is selected from lithium hexamethyl disilazide, sodium hexamethyldisilazide and potassium hexamethyl disilazide.

9. A process according to claim 2, wherein the solvent is selected from the group consisting of a nitrile, a chlorinated hydrocarbon, a polar aprotic solvent, an ester, an ether, a cyclic ether and mixtures thereof.

10. A process according to claim 2, wherein the methylation is carried in the presence of a base.

11. A process according to claim 10, wherein the base is selected from lithium hexamethyl disilazide, sodium hexamethyldisilazide and potassium hexamethyl disilazide.

12. A process according to claim 3, wherein the solvent is selected from the group consisting of a nitrile, a chlorinated hydrocarbon, a polar aprotic solvent, an ester, an ether, a cyclic ether and mixtures thereof.

13. A process according to claim 3, wherein the deprotection is carried in the presence of a base.

14. A process according to claim 13, wherein the base is selected from lithium hexamethyl disilazide, sodium hexamethyldisilazide and potassium hexamethyl disilazide.

15. A process according to claim 4, wherein the solvent is selected from the group consisting of a nitrile, a chlorinated hydrocarbon, a polar aprotic solvent, an ester, an ether, a cyclic ether and mixtures thereof.

16. A process according to claim 4, wherein the reaction is carried in the presence of a base.

17. A process according to claim 16, wherein the base is selected from lithium hexamethyl disilazide, sodium hexamethyldisilazide and potassium hexamethyl disilazide.

18. A process according to claim 5, wherein solvent is selected from the group consisting of a nitrile, a chlorinated hydrocarbon, a polar aprotic solvent, an ester, an ether, a cyclic ether and mixtures thereof.

19. A process according to claim 5, wherein the methylation is carried in the presence of a base.

20. A process according to claim 19, wherein the base is selected from lithium hexamethyl disilazide, sodium hexamethyldisilazide and potassium hexamethyl disilazide.

* * * * *